United States Patent

Wiseman et al.

[11] Patent Number: 5,172,481
[45] Date of Patent: Dec. 22, 1992

[54] ELECTRONIC INCLINOMETER

[75] Inventors: Colin P. Wiseman, Cogenhoe; Paul T. Ryan, Over; Charles W. Wyatt-Millington, Perry, all of United Kingdom

[73] Assignee: The Stanley Works, New Britain, Conn.

[21] Appl. No.: 223,240
[22] PCT Filed: Jan. 23, 1987
[86] PCT No.: PCT/GB87/00042
§ 371 Date: Mar. 14, 1990
§ 102(e) Date: Mar. 14, 1990
[87] PCT Pub. No.: WO87/04515
PCT Pub. Date: Jul. 30, 1987

[30] Foreign Application Priority Data
Jan. 23, 1986 [GB] United Kingdom ............... 8601586

[51] Int. Cl.$^5$ ............................................. G01C 9/06
[52] U.S. Cl. ................................ 33/366; 33/377
[58] Field of Search ...................... 33/366, 365, 377

[56] References Cited
U.S. PATENT DOCUMENTS
4,028,815 6/1977 Buckley et al. .................. 33/366
4,641,434 2/1987 Engler ............................... 33/366

FOREIGN PATENT DOCUMENTS
2070774 9/1981 United Kingdom .............. 33/365
2159628 12/1985 United Kingdom .............. 33/377

Primary Examiner—Harry N. Haroian
Attorney, Agent, or Firm—Chilton, Alix & Van Kirk

[57] ABSTRACT

A sensor for an inclination measuring device which comprises a capsule (3) part-filled with a conductive liquid. First to fourth electrodes (A–D) are disposed within the capsule in contact with the liquid. An electrical signal is applied between electrodes (C, D) and one then the other of electrodes (A, B), to derive a signal indicative of the degree of immersion of the electrode (A), and then the electrode (B) within the liquid. The ratio of these signals is related to the angle of inclination of the capsule about the reference axis O and relative to a first reference angle defined at the gap between the electrodes (A, B). A similar gap, defining a second reference angle is disposed between electrodes (C, D), perpendicular to the gap between electrodes (A, B), and by reconfiguring the electrodes (A–D), to measure the degree of immersion of electrodes (C and D), the sensor is able to sense any angle of inclination about the reference axis.

25 Claims, 7 Drawing Sheets

ELECTRONIC INCLINOMETER

This invention relates to a device and, more particularly, but not exclusively to a sensor for an electronic level or inclination gauge.

Optical levels, more commonly called spirit levels, are well known and provide an optical indication of whether or not a surface is horizontal, based on the principle of an air bubble in a liquid-filled vial always seeking the highest point in the vial, the vial being slightly curved so that when at level, the bubble will always take up an equilibrium position. Such bubble levels, if disposed in a suitable frame, can also be used to provide an indication of whether or not a surface is vertical.

However, such spirit levels are not capable of measuring deviations from horizontal or vertical outside a very limited range. Also, such spirit levels can be difficult to read accurately as the measurement of level or plumb depends on the ability of the user to determine the position of the bubble. Factors such as poor lighting or poor eyesight obviously affect this.

An electronic spirit level has ben proposed by Cantarella, in U.S. Pat. No. 4,167,818, which uses a capsule part-filled with a conductive liquid. Several electrodes are disposed within the capsule, the resistance between the electrodes being dependent on the position of the liquid within the capsule which, in turn, is dependent upon its inclination. A digital readout of angles of inclination from level and from plumb is provided. However, this level, again, is only usable over a limited range of angular deviation from horizontal or vertical.

Capacitive devices, such as that disclosed in EP 35840 have also been proposed. The device of EP 35840 includes a capsule of generally cylindrical form part-filled with a liquid having a dielectric constant different from that of the remainder of the capsule. The capsule is provided with four electrodes, a single, primary, electrode being disposed on one end surface of the capsule and the three other, secondary, electrodes being disposed on the other end surface. Three sensing circuits including three oscillators are provided for sensing the capacitance between the first electrode and the three secondary electrodes.

However, the three secondary electrodes each need a separate processing circuit. As each processing circuit tends to have its own individual characteristics, compensation for this is also necessary. This factor leads to additional manufacturing expense.

According to the invention in a first aspect, there is provided a sensor for an inclination measuring device comprising:

a capsule part-filled with a liquid,
first electrode means comprising first and second electrodes disposed within the capsule, the relative degree of immersion of the first and second electrodes in the liquid being indicative, within a first angular range, of the angle of inclination of the capsule both about a reference axis and relative to a first reference angle.
second electrode means comprising third and fourth electrodes disposed within the capsule, the relative degree of immersion of the third and fourth electrodes in the liquid being indicative, within a second angular range, of the angle of inclination of the capsule both about the reference axis and relative to a second reference angle different from the first reference angle; and
the first and second electrode means being arranged so that angle angle of inclination of the capsule about the reference axis is included within at least one of the first and second ranges and the first and second reference angles are those at which the electrodes of the first and second electrode means, respectively, are substantially equally immersed in the liquid.

According to the invention in a second aspect there is provided an inclination measuring device comprising a capsule part-filled with a liquid, the position of the liquid within the capsule being indicative of the angle of rotation of the capsule about a reference axis, a plurality of electrodes, disposed within the capsule for sensing said position, within an angular range, an excitation source, a sensing circuit and switching means for connecting said electrodes to the sensing circuit and to the excitation source in a plurality of configurations for measuring, sequentially, a plurality of electrical characteristics of the liquid which together are indicative of said position.

An embodiment of the invention will now be described, by way of example, with reference to the accompanying drawings, in which.

Figure 2:
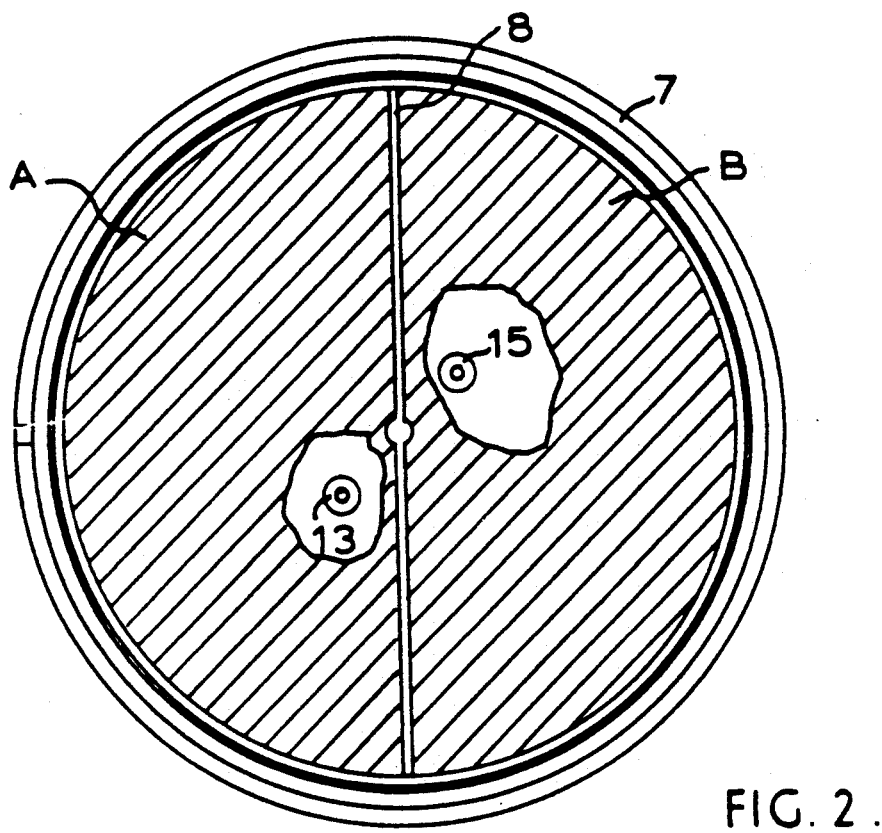
FIG. 2 is a sectional view taken in the plane II—II' of FIG. 1.
Figure 4A:
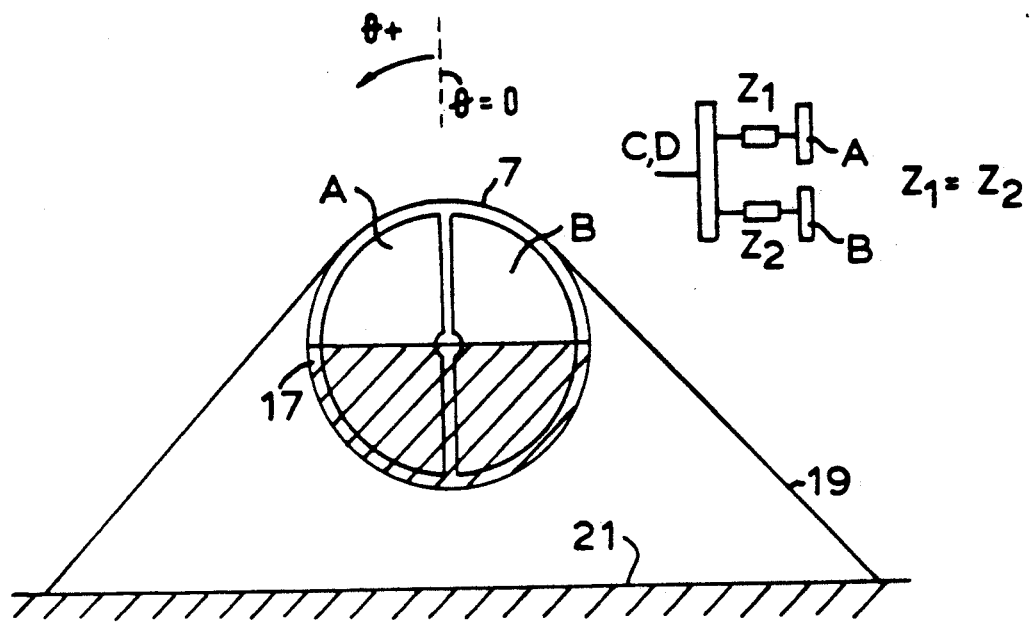
Figure 4B:
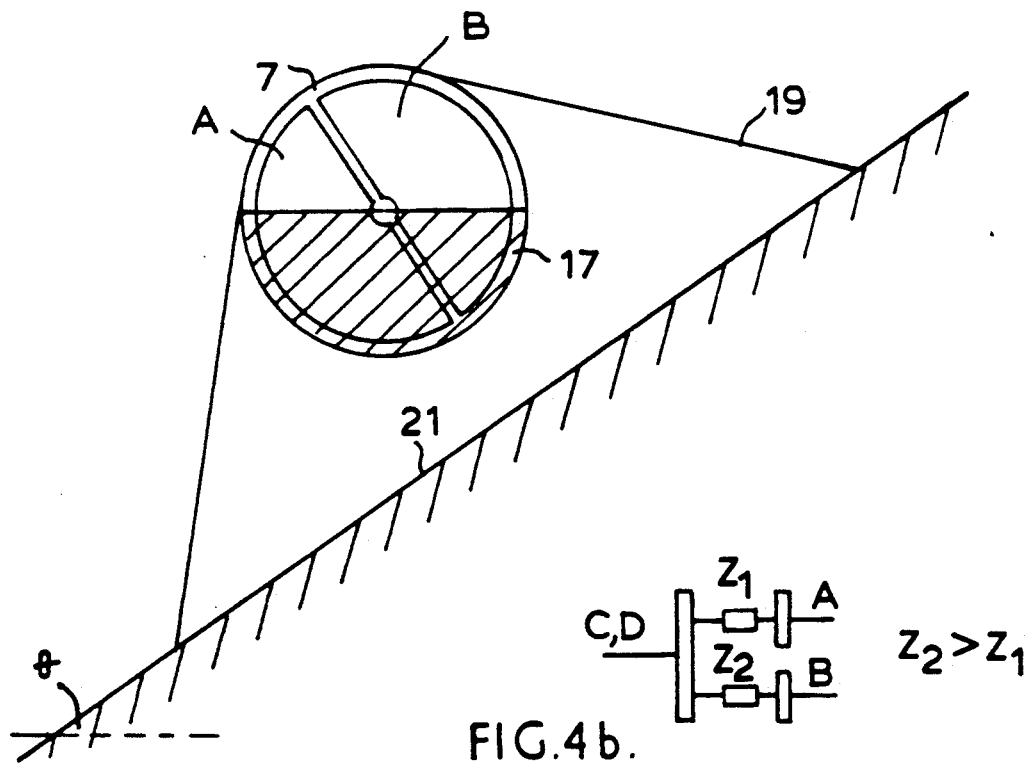
Figure 5A:
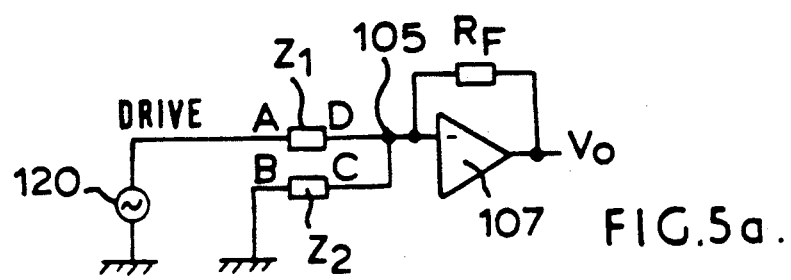
Figure 5B:
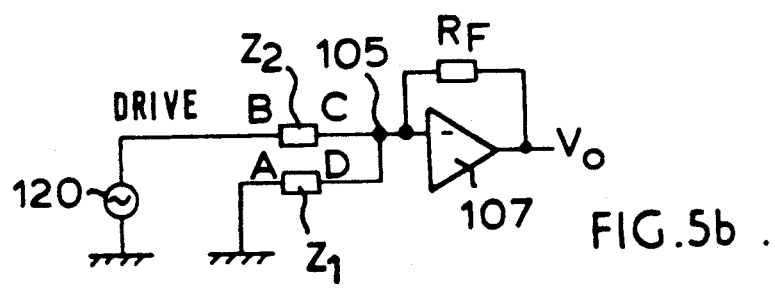
Figure 6:
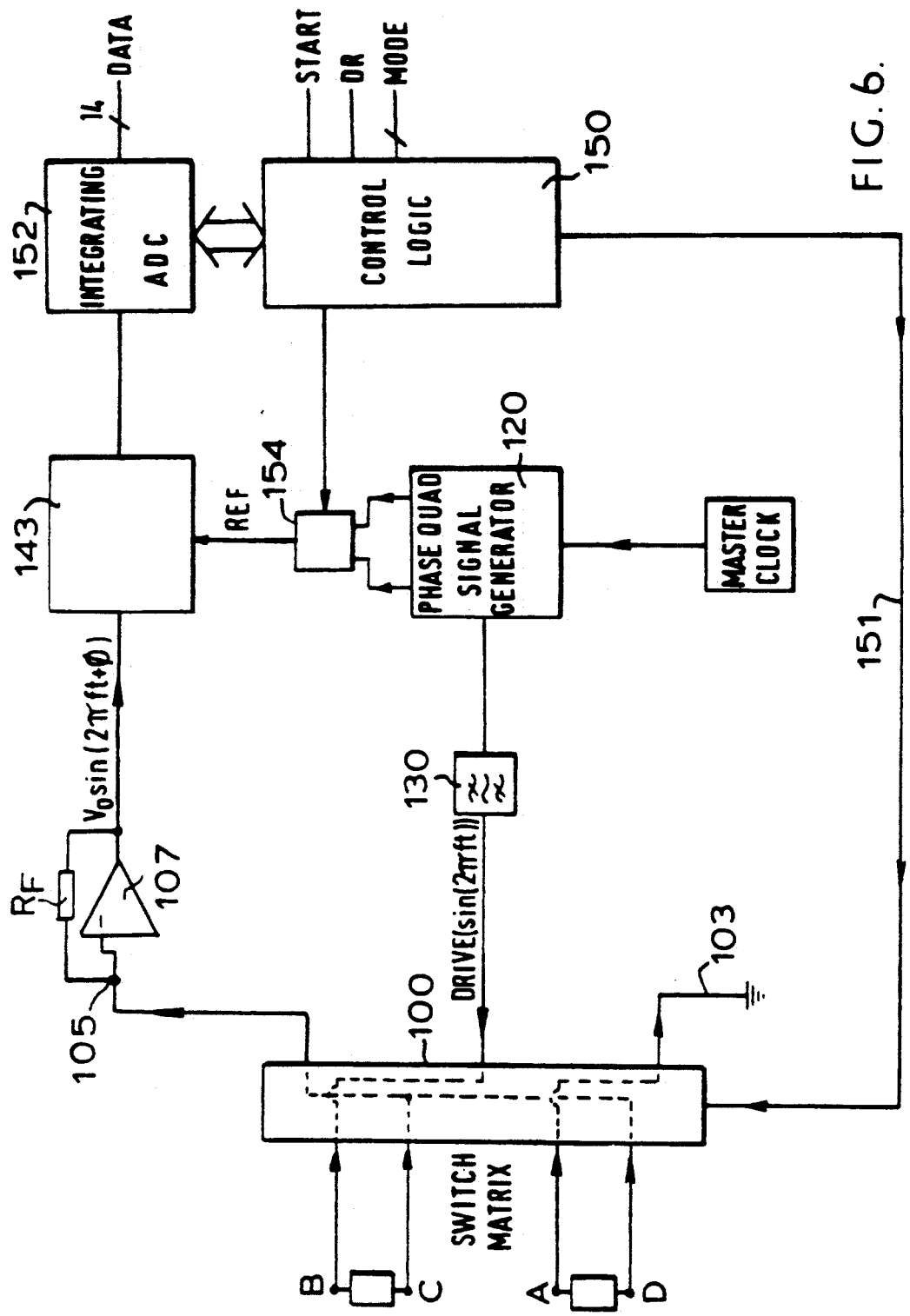
Figure 7:
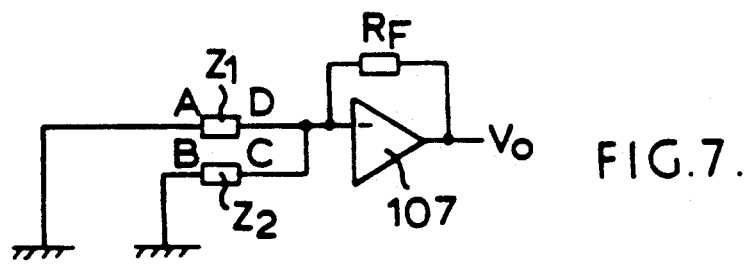
Figure 8A:
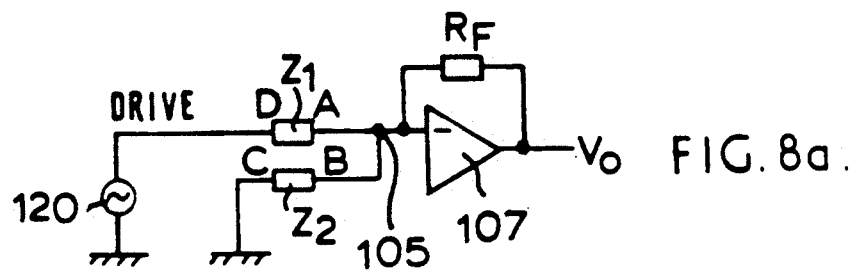
Figure 8B:
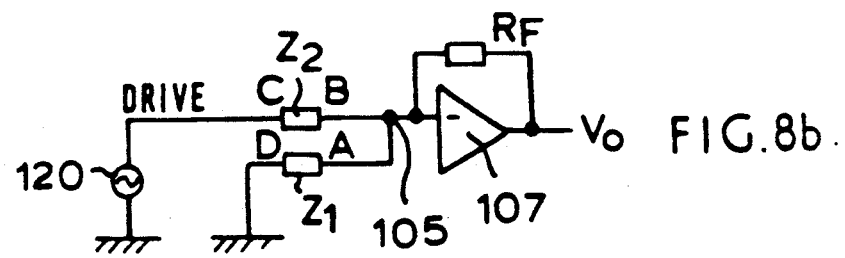
Figure 8C:
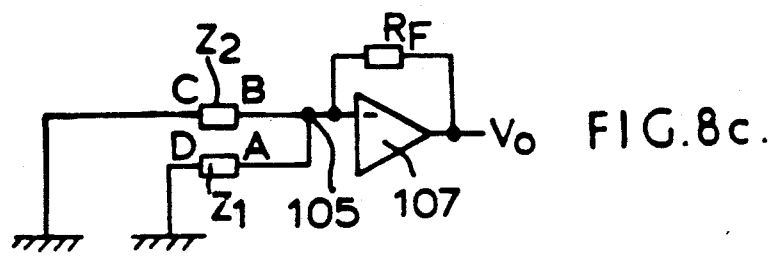
Figure 9:
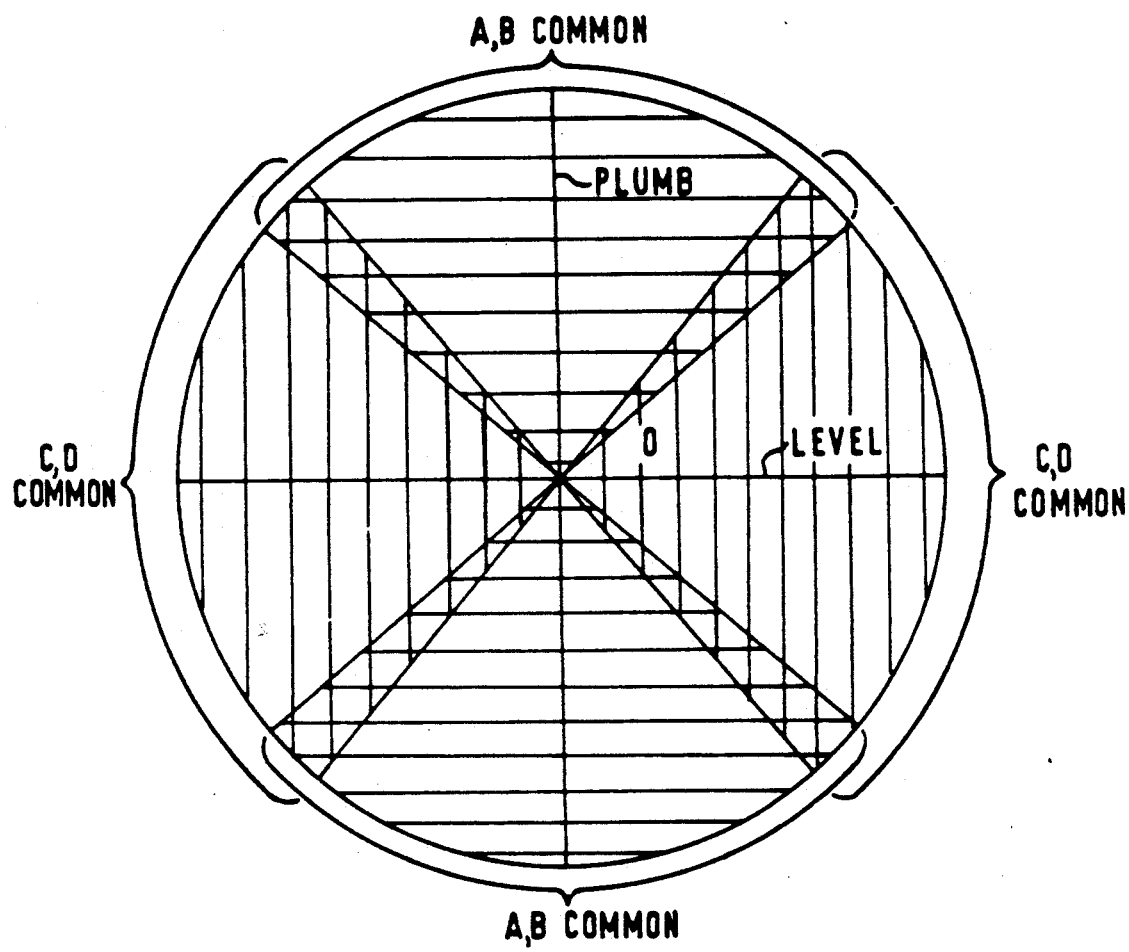

FIGS. 4A-B are sectional views similar to FIG. 2 of the capsule at different inclinations;

FIGS. 5A and 5B show basic configurations of the sensing circuitry for the capsule shown in FIGS. 1 to 4;

FIG. 6 is a block diagram of the general arrangement of the sensing circuitry;

FIG. 7 shows a null measurement arrangement of the circuit shown in FIG. 5;

FIGS 8a, 8b and 8c shows alternative arrangements of the sensing circuitry shown in FIGS. 5 to 7 for use in measuring an alternative range of angles;

FIG. 9 illustrates the angular range of the sensor.

Figure 1:
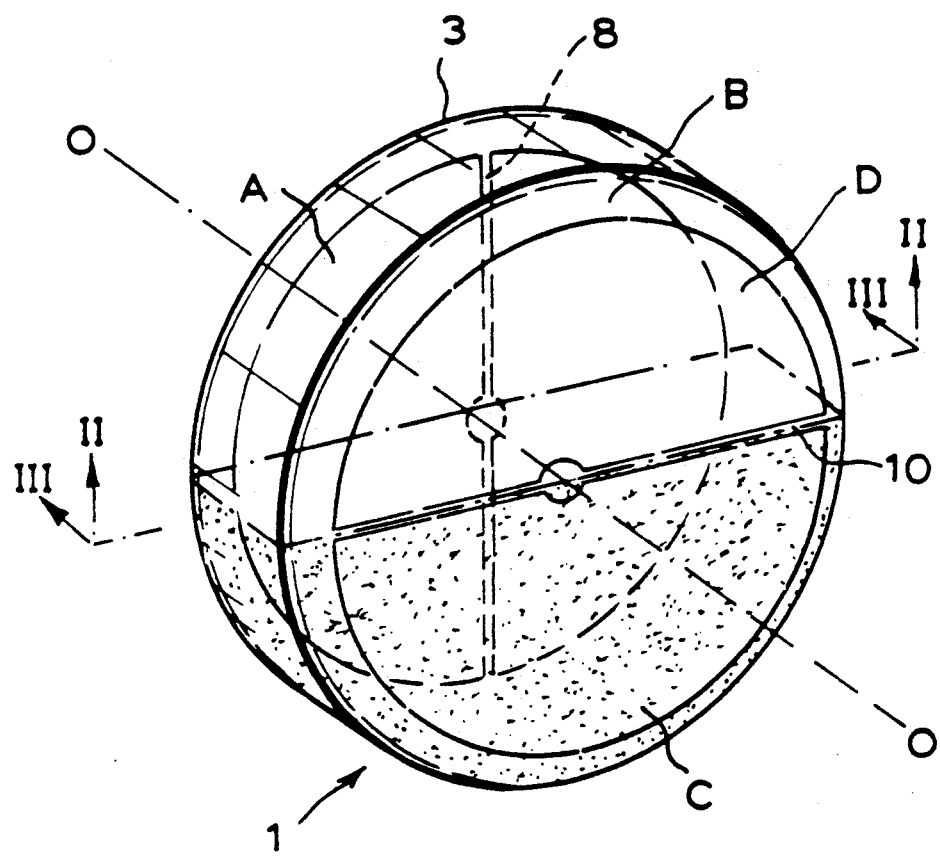
FIG. 1 is a perspective view of a sensor capsule forming part of an embodiment of the invention.
Figure 3:
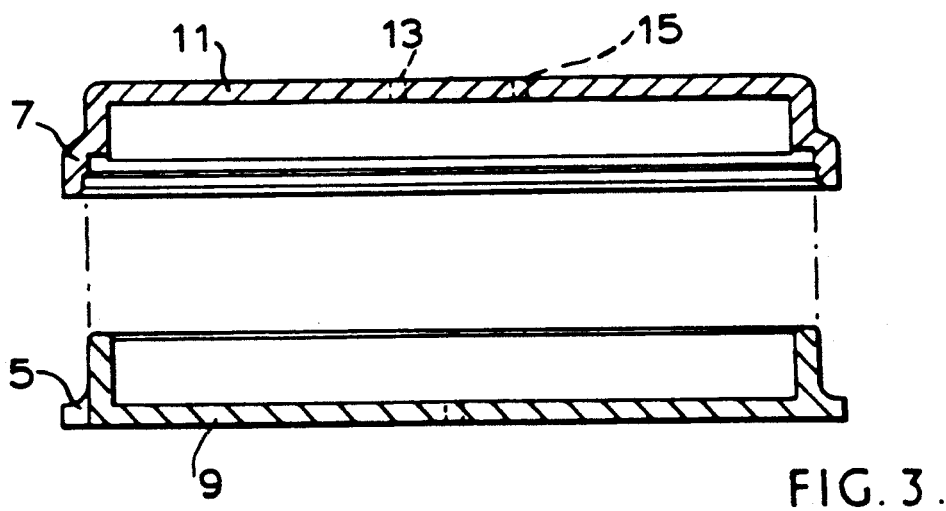
FIG. 3 is an exploded sectional view taken through the plane III—III' of FIG. 1.

Referring to FIGS. 1 to 3, an inclination sensor, generally designated 1 is shown. The sensor comprises a capsule 3 of generally cylindrical form. The capsule 3 is formed from two engageable non-conductive chemically inert plastics mouldings 5,7 formed preferably from thermoplastic polyester (e.g. a polybutylene terephthalate (PBT) for example VALOX) reinforced with 15-20% glass beads to provide strength and stability.

The mouldings 5,7 are ultra-sonically welded together to ensure a hermetic seal. The end faces 9,11 of the mouldings 5,7 are formed of a thickness so as to be elastically deformable in response to pressure variations within the capsule 3, as described hereinafter.

Within mouldings 5,7, electrodes A,B and C,D formed from nickel are respectively disposed. Each electrode A-D is of generally semi-circular form and is formed on its respective moulding 5,7 preferably by vacuum deposition or hot foil blocking (although it is to be appreciated that other electrode-forming methods may be employed). The electrodes A,B (or C,D) are separated one from the other by an elongate gap 8 (or 10) so that the electrodes A,B (or C,D) are not in direct electrical contact. The gaps 8,10 should be narrow, preferably less than 0.5 mm. Connections to the electrodes A-D are provided by means of rivets formed from conductive plastics material, which are bonded, preferably by ultra-sonically welding to the case halves; rivets 13,15 for electrodes A,B are shown in FIG. 2.

Alternatively, the capsule may be formed from two identical plastics discs, the electrodes being formed on the discs by silk screen printing, each disc then being connected to an open axial end of a hollow cylindrical plastics spacer, to form the capsule, the discs being rotated by 90° relative to one another to give the desired electrode configuration shown in FIG. 1.

The electrodes A,B are rotated by 90° about a reference axis O of the capsule with respect to the electrodes C,D to allow measurement of angles through 360° as described hereinafter. A conductive liquid 17 is disposed within the capsule 3, preferably a mixture of distilled water and methanol and a slat, for example sodium acetate trihydrate ($CH_3 COONa\ 3H_2O$), the capsule 3 being filled, at NTP, to half its volume. The remainder of the capsule is filled with air or an inert gas, for example argon.

The general mode of operation of the capsule is described with reference to FIGS. 4A and 4B for which a measurement using electrodes A,B as the sensing electrodes is illustrated. FIGS. 4A and 4B illustrate the capsule 3 in a schematically shown mounting 19 having an edge 21 which is presented to a surface, the inclination of which is to be measured. One pair of electrodes in this case C,D are coupled together to form a common electrode and an alternating voltage is applied in turn to the electrodes A or B. The impedance and, more particularly, the resistance of the path between electrodes C,D and electrode A or electrode B is dependent upon the degree of immersion of electrode A or electrode B in the conductive liquid 17, the larger degree of immersion, the lower the resistance of the path.

Thus by measuring the resistances of the two paths, between electrodes C,D and electrode A and electrodes C,D and electrode B, the angle of inclination $\theta$ of the sensor can be calculated.

More specifically as can be seen by comparison of FIGS. 4A and 4B, the total wetted area of electrodes A,B is always substantially a constant, so that, ignoring cross impedances:

$$\frac{1}{Z_T} = \frac{1}{Z_1} + \frac{1}{Z_2} \qquad 1a$$

where
$Z_T$ = The total resistance of the capsule
$Z_1$ = The resistance of path CD to A
$Z_2$ = The resistance of path CD to B $$\text{and } Z_1 = \frac{180}{90+\theta} \cdot Z_T \qquad 1b$$

$$Z_2 = \frac{180}{90-\theta} \cdot Z_T \qquad 1c$$

So, the ratio, R, of the resistances Z1, Z2 is:

$$\frac{Z_1}{Z_2} = R = \frac{90-\theta}{90+\theta} \qquad 2$$

hence $$\theta = 90 \frac{(1-R)}{(1+R)} \qquad 3$$

Exemplary values of R are as follows:

TABLE 1

| $\theta$ | $R = \frac{Z_1}{Z_2}$ |
|---|---|
| −90 | ∞ |
| −50 | 3.5 |
| −45 | 3 |
| 0 | 1 |
| +45 | 0.33 |
| +50 | 0.286 |
| 90 | 0 |

Circuitry for measuring the resistances $Z_1$, $Z_2$ will now be described with reference to FIG. 5 which shows an operational amplifier 107 in an inverting mode, with feedback resistor $R_F$ being connected between the inverting input terminal and output terminal of the amplifier 107.

Terminals C,D are commoned together and connected to terminal 105 of OP-amp 107; in FIG. 5A, terminal A is connected to A. C. source 120 while terminal B is connected to ground, with these terminals being swapped in FIG. 5B.

Referring to FIG. 5A, assuming $V_{IN} = 1$ volt $$V_{01} = \frac{-AR_F Z_2}{AZ_1 Z_2 + Z_1 R_F + Z_1 Z_2 + Z_2 R_F} \qquad 4$$

and in FIG. 5B $$V_{02} = \frac{-AR_F Z_1}{AZ_2 Z_1 + Z_2 R_F + Z_2 Z_1 + Z_1 R_F} \qquad 5$$

... where A is the open loop gain of the operational amplifier 107.

combining 4 and 5:

$$R = \frac{Z_1}{Z_2} = \frac{V_{02}}{V_{01}} \qquad 6$$

... $V_{01}$, $V_{02}$, $V_{IN}$ being peak amplitudes.

... so that switching of terminals A,B will give a measurement of $V_{01}$ and $V_{02}$ from which R can be calculated which, by Equation 3, will give $\theta$.

A circuit for generating a digital value corresponding to each of these variables is shown in FIG. 6 and includes a switch matrix 100 preferably formed as part of an Application Specific Integrated Circuit (ASIC) connected to electrodes A–D the matrix having further connections to: an input terminal having a drive input waveform applied from signal generator 120 via band pass filter 130 of the form sin (1πft) (t=time (secs) : f=frequency (Hertz)), an earth connection 103 and an output terminal connected to operational amplifier 107. The switching functions of the matrix 100 are controlled by control logic circuitry 150 via control bus 151 Electrode configuration instructions are sent to the control logic from computing circuitry (not shown) via the MODE lines. Connections equivalent to that illustrated in FIG. 5b are shown in phantom lines.

Use of the switch matrix allows common excitation source and sensing circuitry to be used for all electrode configurations (which are described below), thus reducing potential excitation and sensing circuitry inaccuracies.

The output from operational amplifier 107 is fed to a multiplier 143. The multiplier 143 is connected to an integrating analog to digital converter 152 which integrates the output of the multiplier and converts the integrated signal into a 14 bit digital signal, which is output to computing circuitry (not shown) for calculation of the inclination angle.

The multiplier 143 is also supplied with reference signals from the signal generator 120. The reference signals comprise two outputs (Phase and Quad) of the same frequency as the drive waveform and in phase quadrature with one another ($\sin(2\pi ft)$, $\cos(2\pi ft)$). Phase and Quad need not be in phase with the drive signal. These signals are alternately supplied to the multiplier 143 through a switch 154 controlled by control logic unit 150.

The multiplier acts to multiply the waveform input from amplifier 107 (generally of the form $A \sin(2\pi ft + \phi)$) by the chosen reference signal so that its output is, sequentially:

$$V_0 \sin(2\pi ft + \phi) \cdot \sin(2\pi ft) \quad \quad 12a$$

$$V_0 \sin(2\pi ft + \phi) \cdot \cos(2\pi ft) \quad \quad 12b$$

The signals represented by equations 12A and 12B are integrated over n cycles of the signal waveform (N being an integer) with respect to time by integrator 152, giving:

$$\int V_0 \sin(2\pi ft + \phi) \cdot \sin 2\pi ft = KV_0 \cos \phi \quad \quad 13a$$

$$\int_N^N V_0 \sin(2\pi ft + \phi) \cdot \cos 2\pi ft = KV_0 \sin \phi \quad \quad 13b$$

$K = $ Constant

The circuit provides a 14 bit output proportional to these values. As can be seen, squaring 13A and 13B and adding gives:

$$K^2 V_0^2 \cos^2\phi + K^2 V_0^2 \sin^2\phi + K^2 V_0^2$$

... which is proportional to $V_o^2$ and thus proportional to the square of the amplitude of the signal input to multiplier 143.

The multiplier may be replaced by logic, which gates the input signal from op amp 107 with a reference signal which pulses on, then off, at half cycle intervals of the drive signal $\sin(2\pi ft)$. Gating the input signal in this way has the same effect as multiplying the input signal by a sinusoidal signal of the same frequency as the device signal provided that the input signal is substantially free from harmonics and D. C. terms. Gating the input signal, alternately, with two such reference signals in phase quadrature will then provide the two outputs of equations 12a and b.

In an alternative configuration, a single reference signal ($\sin 2\pi ft$) which is in phase with the drive signal ($\sin 2\pi ft$) may be applied to multiplier 143. The resulting multiplied output will then only contain components of the waveform input from Op Amp 107 which are independent of the arbitrary phase $\Phi$ (effectively $\Phi=0$ for this measurement) so that, with reference to equation 13a, the integrated output will be $KV_o \cos 0 = KV_o$, so a quadrature measurement is unnecessary.

In order to compensate for DC offsets present in the circuitry, and coherent noise pickup, the control logic is also operable in a calibration (NULL) mode, for measuring of the offset prior to each resistance measurement. For this, the circuitry is configured as shown in FIG. 7, with terminals A,B both being connected to ground or another known potential and the offset $V_{o1n}$ (or $V_{o2n}$ which is equivalent to $V_{o1n}$) being measured as appropriate.

In all, the following sequence of events (initiated in response to a start signal (START) from the computing circuitry) is required for one inclination measurement to be made:

TABLE 2

| Measurement | Measured quantity |
| --- | --- |
| NULL | $V_{01N}$ |
| $Z_1$ Phase | $V_{01P} + V_{01N}$ |
| $Z_1$ Quad | $V_{01Q} + V_{01N}$ |
| NULL | $V_{01N}$ |
| $Z_2$ Phase | $V_{02P} + V_{02N}$ |
| $Z_2$ Quad | $V_{02Q} + V_{02N}$ |

Alternatively, if the drive and reference signals are in phase, as previously described, only the measurement of $Z_1$ phase and $Z_2$ phase a NULL are necessary.

When a measurement is finished, the control logic sends a signal to the computing circuitry by means of the data ready (DR) line.

Electrodes A,B are used for sensing angles up to $\pm 50°$ from the horizontal in the configuration illustrated in FIGS. 4A and 4B. For angles of inclination greater than these limits, the control logic reconfigures the electrodes so that the electrodes A,B become the common electrode and the orthogonally disposed electrodes C,D become the sensing electrodes, the sensor measuring angles in this configuration in the range $\pm 50°$ from vertical. The electrode configuration for these measurements, together with the offset configuration are shown in FIG. 8A-C. The sequence of events for the measurement of inclination for the electrodes in this configuration is analogous to that previously described with reference to Table 2.

Use of such electrode switching allows a full 360° of inclination angle to be measured, in terms of deviation from level or plumb, (as shown in FIG. 9) with the electrode configuration being chosen by the computing and control circuitry in accordance with the angle of inclination of the sensor. When initializing an inclination measurement, the processing circuitry performs a measurement with an arbitrary pair of electrodes e.g. C,D chosen as the common pair as shown in FIGS. 5a, 5b and 7. If the ratio R calculated by the computing circuitry is within an allowable range corresponding to $\pm 50°$ (see Table 1), the measurement proceeds whereas if the measured ratio is outside the allowable range, the configuration is changed to that shown in FIG. 8 and the measurement is then performed.

The inventors have found that the sensor described is subject to some measurement inaccuracies, which can be expressed in terms of measured angle $\theta$ and actual angle $\theta$ as follows:

$$\theta = a^* \theta' + b$$

Where $a^*$ is a function principally of any variation in initial liquid level with respect to the measuring electrodes, although other factors include the dimensions of the gap between the electrodes A and B (or C and D), and the resistance of the switches in the switch matrix; b is dependent upon manufacturing tolerance.

$\theta'$ is effectively zero when both sensing electrodes are equally immersed in the liquid, so that the capsule will have the greatest inherent accuracy at this position. The orthogonal disposition of the electrode pair A,B relative to electrode pair C,D gives the capsule two maximum accuracy positions which, in the described embodiments, are chosen to be level and plumb thus allowing measurements of maximum accuracy to be made at the most often measured angular positions, although the disposition of the electrode pairs may be chosen to give different maximum accuracy positions for specific application.

We claim:

1. A sensor for an inclination measuring device comprising:
   a capsule part-filled with a liquid,
   first electrode means comprising first and second electrodes disposed within the capsule, the relative degree of immersion of the first and second electrodes in the liquid being indicative, within a first angular range, of the angle of inclination of the capsule both about a reference axis and relative to a first reference angle.
   second electrode means comprising third and fourth electrode disposed within the capsule, the relative degree of immersion of the third and fourth electrodes in the liquid being indicative, within a second angular range, of the angle of inclination of the capsule both about the reference axis and relative to a second reference angle different from the first reference angle; and
   the first and second electrode means being arranged so that any angle of inclination of the capsule about the reference axis is included within at least one of the first and second ranges and the first and second reference angles are those at which the electrodes of the first and second electrode means, respectively, are substantially equally immersed in the liquid.

2. A sensor as claimed in claim 1 wherein the first and second reference angles are othogonally disposed.

3. A sensor as claimed in claim 1 wherein the first and second electrodes are of substantially semi-circular form and are spaced one from the other about the reference axis.

4. A sensor as claimed in claim 1 wherein the third and fourth electrodes are of semi-circular form and are spaced one from the other about the reference axis.

5. An inclination measuring device including a sensor as claimed in claim 1, the sensor being mounted relative to a measuring surface disposed parallel to the reference axis, so that inclination of the measuring surface results in corresponding inclination of the sensor capsule.

6. A device as claimed in claim 5 further comprising:
   a drive source for generating a drive signal to be applied to the capsule,
   processing means for processing an output signal from the capsule,
   switch means, arranged to select any one of the electrodes and to connect the selected electrode to the drive source whereby the drive signal is applied to the capsule through the selected electrode, the drive signal being modified by the impedance of the liquid between the selected electrode and a common electrode to form the output signal, the impedance being dependent upon the degree of immersion of the selected electrode in the liquid, and
   control means, for controlling the operation of the switch means.

7. A device as claimed in claim 6 wherein the switch means is arranged to configure the electrodes so that the electrodes of the electrode means which does not include the selected electrode are connected together to form the common electrode.

8. A device as claimed in claim 6 wherein the switch means is arranged to select one, then the other, of the electrodes of one said electrode means as said selected electrode and to connect the non-selected electrode of the said one electrode means to ground.

9. A device as claimed in claim 8 wherein the drive source generates an alternating electrical drive signal.

10. A device as claimed in claim 9 wherein the processing means comprises:
    amplifier means for amplifying the output signal,
    multiplier means, for multiplying the amplified signal, sequentially, by first and second reference signals, to generate first and second multiplied signals, the first and second reference signals including a component having the same frequency as the drive signal and the reference signals being in phase quadrature with one another: and
    integrating means, for integrating each multiplied signal over a predetermined number of cycles of the multiplied signal to form first and second integrated signals; and
    calculation means, responsive to the integrating means, for deriving the inclination angle from the integrated signals associated with the sequentially selected electrodes.

11. A device as claimed in claim 10 wherein the multiplier means gates the amplified signal in accordance with the reference signals which each pulse on then off at half cycle intervals of the drive signal.

12. A device as claimed in claim 9 wherein the processing means comprises:
    amplifier means, for amplifying a said modified signal,
    multiplier means for multiplying the amplified signal by a reference signal including a component in phase with and of the same frequency as the drive signal to form a multiplied signal; and
    integrating means for integrating the output of the multiplier means over a predetermined number of cycles of the signal, to form an integrated signals; and
    calculation means, responsive to the integrating means, for deriving the inclination angle from the integrated signals associated with the sequentially selected electrodes.

13. A device as claimed in claim 12 wherein the multiplier means gates the amplified signal with the reference signal, the reference signal pulsing on then off at half cycle intervals of the drive signal.

14. A device as claimed in claim 10 wherein the measuring means further comprises an analog-to-digital converter, for converting the output of the integrating means into a digital signal.

15. A device as claimed in claim 10 wherein the control means is responsive to the processing means to select the electrodes of the first or second electrode means so that the angle of inclination to be measured lies within the respective range of the first or second electrode means.

16. A device as claimed in claim 7 wherein the switch means further configures the electrodes in an offset measuring configuration in which either the first and second or the third and fourth electrodes are connected together to form the common electrode and the common electrode is connected to the measuring means and the non-commonly connected electrodes are set to a known potential.

17. A device as claimed in claim 15 wherein the switch means is arranged to be configured in the DC offset measuring configuration between every electrode selection.

18. An inclination measuring device comprising a capsule part-filled with a liquid, the position of the liquid within the capsule being indicative of the angle of rotation of the capsule about a reference axis, a plurality of electrodes disposed within the capsule for sensing said position within an angular range, an excitation source, a sensing circuit and switching means for connecting said electrodes to the sensing circuit and to the excitation source in a plurality of configurations for measuring, sequentially, a plurality of electrical characteristics of the liquid which together are indicative of said position.

19. A device as claimed in claim 18 wherein said switch means comprises a switch matrix.

20. A device as claimed in claim 19 wherein said switch matrix forms part of an integrated circuit.

21. A device as claimed in claim 18 wherein the switch means is arranged to select any one of the electrodes and to connect the selected electrode to the excitation source whereby a drive signal is applied to the capsule through the selected electrode, the drive signal being modified by the impedance of the liquid between the selected electrode and a common electrode, which is connected to the sensing circuit to form the output signal, and said impedance is dependent upon the degree of immersion of the selected electrode in the liquid.

22. A device as claimed in claim 21 wherein said plurality of electrodes includes a first pair of electrodes and a second pair of electrodes, the switch means being arranged to configure the electrodes so that the electrodes of the pair which does not include the selected electrode are connected together to form the common electrode and to connect the so formed common electrode to the sensing circuit.

23. A device as claimed in claim 21 wherein the switch means is arranged to select one then the other of the electrodes of one said electrode pair as said selected electrode and to connect the non-selected electrode of the electrode pair to ground.

24. A device as claimed in claim 18 wherein said plurality of electrodes are each of substantially semi-circular form and are arranged in pairs, the electrodes of each pair being spaced one from the other about the reference axis.

25. A device as claimed in claim 18 wherein said angular range is 360°.

* * * * *